US008607921B2

(12) United States Patent
Berker et al.

(10) Patent No.: US 8,607,921 B2
(45) Date of Patent: *Dec. 17, 2013

(54) HEARING PROTECTION PROCESS AND DEVICE

(75) Inventors: Ali Berker, Saint Paul, MN (US); Sharon R Garber, Plymouth, MN (US); Richard W. Greger, Saint Paul, MN (US); Marie Aloshyna ep Lesuffleur, Woodbury, MN (US); Smarajit Mitra, West Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 272 days.

This patent is subject to a terminal disclaimer.

(21) Appl. No.: 13/140,309

(22) PCT Filed: Dec. 16, 2009

(86) PCT No.: PCT/US2009/068214

§ 371 (c)(1),
(2), (4) Date: Jun. 16, 2011

(87) PCT Pub. No.: WO2010/075128

PCT Pub. Date: Jul. 1, 2010

(65) Prior Publication Data

US 2011/0253153 A1   Oct. 20, 2011

Related U.S. Application Data

(60) Provisional application No. 61/140,388, filed on Dec. 23, 2008.

(51) Int. Cl.
*H04R 25/00* (2006.01)
(52) U.S. Cl.
USPC .......................... 181/129; 181/284; 181/286
(58) Field of Classification Search
USPC .......................................... 181/129, 284, 286
See application file for complete search history.

(56) References Cited

U.S. PATENT DOCUMENTS 5,188,123 A   2/1993   Gardner, Jr.
5,203,352 A   4/1993   Gardner, Jr.
(Continued)

FOREIGN PATENT DOCUMENTS

JP   2006-106211   4/2006
JP   2006-257993   9/2006
JP   2007-015292   1/2007

OTHER PUBLICATIONS

Sigalas, M., et al., "Classical vibrational modes in phononic lattices: theory and experiment," Z. Kristallogr, vol. 220, pp. 765-809 (2005).
J.O. Vasseur, P.A. Deymier, A. Khelif, Ph. Lambin, B. Dajfari-Rouhani, A. Akjouj, L. Dobrzynski, N. Fettouhi, and J. Zemmouri, "Phononic crystal with low filling fraction and absolute acoustic band gap in the audible frequency range: A theoretical and experimental study," Phys. Rev. E 65, 056608-1-056608-6 (May 2, 2002).
Goffaux et al., "Comparison of the sound attenuation efficiency of locally resonant materials and elastic band-gap structures," Physical Review B, vol. 70, 184302-1-184302-6 (Nov. 18, 2004).

(Continued)

*Primary Examiner* — Forrest M Phillips
(74) *Attorney, Agent, or Firm* — Craig A. Deutsch

(57) ABSTRACT

A hearing protection process comprises (a) providing at least one hearing protection device comprising at least one sound barrier comprising at least one substantially periodic array of structures disposed in a first medium having a first density, the structures being made of a second medium having a second density different from the first density, wherein one of the first and second media is a viscoelastic medium having a speed of propagation of longitudinal sound wave and a speed of propagation of transverse sound wave, the speed of propagation of longitudinal sound wave being at least about 30 times the speed of propagation of transverse sound wave, and wherein the other of the first and second media is a viscoelastic or elastic medium; and (b) interposing the hearing protection device between an acoustic source and an acoustic receiver in the form of a human ear.

20 Claims, 2 Drawing Sheets

(56) References Cited

U.S. PATENT DOCUMENTS

| | | | |
|---|---|---|---|
| 5,678,363 A * | 10/1997 | Ogorchock et al. | 52/144 |
| 5,792,998 A | 8/1998 | Gardner, Jr. et al. | |
| 6,119,807 A * | 9/2000 | Benson et al. | 181/208 |
| 7,249,653 B2 * | 7/2007 | Sheng et al. | 181/290 |
| 7,263,028 B2 * | 8/2007 | Thomas et al. | 367/1 |
| 7,837,008 B1 * | 11/2010 | Lane et al. | 181/284 |
| 8,132,643 B2 * | 3/2012 | Berker et al. | 181/210 |
| 8,276,709 B2 * | 10/2012 | Berker et al. | 181/286 |
| 2003/0062012 A1 | 4/2003 | Homsi et al. | |
| 2005/0283882 A1 | 12/2005 | Berger et al. | |
| 2007/0143907 A1 | 6/2007 | Hansson et al. | |
| 2008/0264715 A1 | 10/2008 | Leong et al. | |
| 2011/0100746 A1 * | 5/2011 | Berker et al. | 181/286 |

OTHER PUBLICATIONS

Hsu et al., "Lamb waves in binary locally resonant phononic plates with two-dimensional lattices," Applied Physics Letters, vol. 90, No. 20, pp. 201904-1-201904-3, ISSN: 0003-6951 (May 15, 2007).

Olivieri et al., "Measurement of transmission loss of materials using a standing wave tube," Inter-Noise 2006, Dec. 3-6, 2006, Honolulu, Hawaii USA.

Ph. Lambin, A. Khelif, J.O. Vasseur, L. Dobrzynski, and B. Djafari-Rouhani, "Stopping of acoustic waves by sonic polymer-fluid composites," Phys. Rev. E, vol. 63, pp. 066605-1-066605-6 (May 22, 2001).

U.S. Department of Transportation, Federal Aviation Administration, Advisory Circular No. 25.856-1, Thermal/Acoustic Insulation Flam Propagation Test Method Details,' Jun. 24, 2005.

J.O. Vasseur et al., "Experimental evidence for the existence of absolute acoustic band gaps in two-dimensional periodic composite media", Journal Physics: Condens, Matter 10, PII: S0953-8984(98)93210-6, pp. 6051-6064 (Apr. 9, 1998).

* cited by examiner

HEARING PROTECTION PROCESS AND DEVICE

STATEMENT OF PRIORITY

This application claims the priority of U.S. Provisional Application No. 61/140,388, filed Dec. 23, 2008, the contents of which are hereby incorporated by reference.

FIELD

This invention relates to acoustic hearing protection processes and, in another aspect, to devices for use in providing sound attenuation or insulation therein.

BACKGROUND

Environmental sounds typically comprise a mixture of various sound wave frequencies having varying intensities. Repeated or prolonged exposure of human ears to environmental sounds of sufficiently high sound pressure levels can cause temporary or permanent hearing loss. For example, noises resulting from explosions or bursts often comprise sound wave frequencies that can be in both relatively high and low frequency bands and can have an intensity sufficient to cause hearing problems.

Individuals who are frequently exposed to sounds of dangerous frequencies and intensities run the risk of incurring hearing loss or even deafness. These individuals include workers at demolition or construction sites, operators of noisy equipment, and personnel in active military service. Ear (that is, hearing) protection devices are often desired to reduce or prevent a loss in hearing acuity and the gradual increase in the threshold of hearing that can result from extended exposure to loud noise.

Various sound attenuation devices are known that specifically address this problem. These include conventional earplug devices, earmuff devices, and the like, which function to reduce the negative effects of noise exposure by limiting the entry of sound waves into the ear. Earmuff devices can be preferred over earplug devices, due to their greater ease of intermittent use (where repeated insertion and removal of earplugs would be annoying or impractical) and/or superior comfort (for example, due to the use of soft ear cushions and the absence of items inserted into the ear).

Conventional earmuff devices generally include a pair of rigid earcups connected by a head band, with foam padding inside the earcups (for sound absorption) and around the rims of the earcups (for comfort and acoustic sealing). In order to obtain a perceptible and effective level of sound attenuation, the foam padding is generally fairly thick (for example, about 1-2 centimeters thick). This adds bulk or volume, as well as mass or weight, to the earmuff device, further necessitating thick-profile, large earcups and a resulting larger and heavier earmuff device that can be inconvenient and/or uncomfortable (for example, hot and sweat-inducing) for the wearer. This has often led to a lack of compliance with hearing protection guidelines and/or regulations and to resulting hearing damage.

Furthermore, in some environments (for example, extremely loud industrial or manufacturing plants, construction or demolition sites, and the like), very high sound attenuation can be desired from earmuff devices. Numerous attempts to increase earmuff sound attenuation have been made, including, for example, reducing acoustic leaks through or around earcups, increasing the mass and/or volume of the earcups, increasing head band tension, and minimizing resonating surfaces such as flat surfaces. These attempts have been at least somewhat successful in increasing sound attenuation, but the resulting earmuff devices have been heavier, larger, more difficult to put in place, and/or generally less comfortable than the original earmuff devices, as well as often unacceptably attenuating desirable acoustic frequencies (for example, the relatively high frequencies of human speech, warning signals, and the like) along with (or even to a greater extent than) undesirable acoustic frequencies.

SUMMARY

Thus, we recognize that there is a need for hearing protection processes that can provide a relatively high level of sound attenuation or insulation (reducing sound transmission) by using hearing protection devices (for example, earmuff devices) that are relatively small in external dimensions and/or relatively light in weight. Preferably, the devices can be at least partially effective over a relatively broad range of audible acoustic frequencies and/or can be relatively simply and cost-effectively prepared.

Briefly, in one aspect, this invention provides such a process, which comprises (a) providing at least one hearing protection device comprising at least one sound barrier comprising at least one substantially periodic array of structures disposed in a first medium having a first density, the structures being made of a second medium having a second density different from the first density, wherein one of the first and second media is a viscoelastic medium having a speed of propagation of longitudinal sound wave and a speed of propagation of transverse sound wave, the speed of propagation of longitudinal sound wave being at least about 30 times the speed of propagation of transverse sound wave, and wherein the other of the first and second media is a viscoelastic or elastic medium; and (b) interposing the hearing protection device between an acoustic source (preferably, a source of audible acoustic frequencies) and an acoustic receiver in the form of a human ear. Preferably, the hearing protection device is an acoustic earmuff device, and/or the substantially periodic array of structures is a one-dimensional array in the form of a multi-layer structure comprising alternating layers of the first and second media.

It has been discovered that, by selecting viscoelastic materials having certain characteristics and combining them with viscoelastic or elastic materials to form spatially periodic arrays, phononic crystal structure band gaps or at least significant transmission losses (for example, greater than 20 decibels (dB)) can be obtained in at least portions of the audible range (that is, the range of 20 hertz (Hz) to 20 kilohertz (kHz)). Such structures can be relatively light in weight and relatively small (for example, having external dimensions on the order of a few centimeters or less).

The phononic crystal structures can generate acoustic band gaps in a passive, yet frequency selective way. Unlike the most common sound absorbers used in the acoustics industry, phononic crystals control sound in transmission mode. Within the range of frequencies of the band gap, there can be essentially no transmission of an incident sound wave through the structure. The band gap is not always absolute (that is, no sound transmission), but the sound transmission loss can often be on the order of 20 decibels (dB) or more. In the acoustic industry, attenuations on the order of 3 dB are considered significant, so 20+ dB is a very significant loss in transmission, approaching 100 percent reduction in acoustic power.

Thus, if desired for certain applications, phononic crystal structures can be placed between a sound source and a receiver to allow only select frequencies to pass through the structure. The receiver thus hears filtered sound, with undesirable frequencies being blocked. By properly configuring the phononic crystal structure, the transmitted frequencies can be focused at the receiver, or the undesirable frequencies can be reflected back to the sound source (much like a frequency selective mirror). Unlike current acoustic materials, the phononic crystal structures can be used to actually manage sound waves, rather than simply to attenuate or reflect them.

By controlling such design parameters as the selection of materials, the type of lattice structure, the spacing of the different materials, and so forth, the frequency of the band gap, the number of gaps, and their widths can be tuned, or, at a minimum, the transmission loss levels can be adjusted as a function of frequency. Thus, the phononic crystal structures also can be designed to provide a relatively flat response across a selected frequency range, if desired, so as to allow for at least some transmission of desirable acoustic freqencies (for example, the relatively high frequencies of human speech, warning signals, and the like).

Surprisingly, the phononic crystal structures, when included in a hearing protection device (preferably, within the earcups of an acoustic earmuff device), can provide sound attenuation at selective frequency bands (for example, 500-800 Hertz and 1000-4000 Hertz) essentially as effectively as (or even better than) the relatively much thicker (for example, relatively close to an order of magnitude thicker) foam pads conventionally used in acoustic earmuff devices. This can provide a relatively low-profile, broad-band hearing protection device, which, in at least some embodiments, can meet the above-cited need for hearing protection devices that can be at least partially effective at audible acoustic frequencies (surprisingly, even at audible frequencies below about 1000 Hertz) while being relatively small in external dimensions and/or relatively light in weight. The hearing protection process of the invention can be used to provide hearing protection in a variety of different environments including industrial, construction, and recreational environments, and the like.

In another aspect, this invention also provides a hearing protection device comprising (a) at least one sound barrier comprising at least one substantially periodic array of structures disposed in a first medium having a first density, the structures being made of a second medium having a second density different from the first density, wherein one of the first and second media is a viscoelastic medium having a speed of propagation of longitudinal sound wave and a speed of propagation of transverse sound wave, the speed of propagation of longitudinal sound wave being at least about 30 times the speed of propagation of transverse sound wave, and wherein the other of the first and second media is a viscoelastic or elastic medium; and (b) at least one casing that at least partially encloses the sound barrier and is adapted for contact with the human ear. Preferably, the hearing protection device is an acoustic earmuff device, and/or the substantially periodic array of structures is a one-dimensional array in the form of a multi-layer structure comprising alternating layers of the first and second media.

BRIEF DESCRIPTION OF DRAWING

These and other features, aspects, and advantages of the present invention will become better understood with regard to the following description, appended claims, and accompanying drawing, wherein:

DETAILED DESCRIPTION

Sound Barrier Materials

Figure 1:
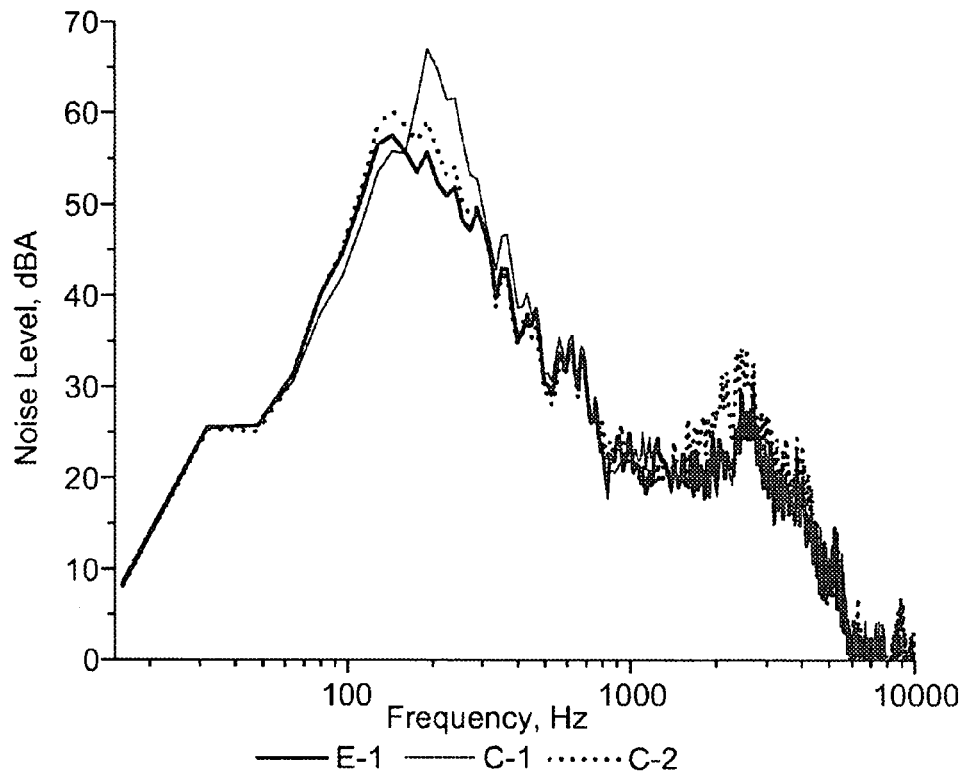
FIG. 1 is a plot of sound pressure (or noise) level (in dBA; that is, units of the A-weighted decibel scale) versus frequency (in Hz) for the embodiment of the process (and device) of the invention described in Example 1 and for the comparative processes (and devices) of Comparative Examples 1 and 2.

Materials that are suitable for use as the above-referenced viscoelastic components of the sound barrier of the process of the invention include those viscoelastic solids and liquids having (preferably, at least in the audible range of acoustic frequencies) a speed of propagation of longitudinal sound wave that is at least about 30 times (preferably, at least about 50 times; more preferably, at least about 75 times; most preferably, at least about 100 times) its speed of propagation of transverse sound wave. Useful viscoelastic solids and liquids include those having a steady shear plateau modulus ($G°_N$) of less than or equal to about $5\times10^6$ Pascals (Pa) at ambient temperatures (for example, about 20° C.), the steady shear plateau modulus preferably extending from about 30 Kelvin degrees to about 100 Kelvin degrees above the glass transition temperature ($T_g$) of the material. Preferably, at least one of the viscoelastic materials in the sound barrier has a steady shear plateau modulus of less than or equal to about $1\times10^6$ Pa (more preferably, less than or equal to about $1\times10^5$ Pa) at ambient temperatures (for example, about 20° C.).

Examples of such viscoelastic materials include rubbery polymer compositions (for example, comprising lightly-crosslinked or semi-crystalline polymers) in various forms including elastomers (including, for example, thermoplastic elastomers), elastoviscous liquids, and the like, and combinations thereof (preferably, for at least some applications, elastomers and combinations thereof). Useful elastomers include both homopolymers and copolymers (including block, graft, and random copolymers), both inorganic and organic polymers and combinations thereof, and polymers that are linear or branched, and/or that are in the form of interpenetrating or semi-interpenetrating networks or other complex forms (for example, star polymers). Useful elastoviscous liquids include polymer melts, solutions, and gels (including hydrogels).

Preferred viscoelastic solids include silicone rubbers (preferably, having a durometer hardness of about 20 A to about 70 A; more preferably, about 30 A to about 50 A), (meth)acrylate (acrylate and/or methacrylate) polymers (preferably, copolymers of isooctylacrylate (IOA) and acrylic acid (AA)), block copolymers (preferably, comprising styrene, ethylene, and butylene), cellulosic polymers (preferably, cork), blends of organic polymer (preferably, a polyurethane) and polydiorganosiloxane polyamide block copolymer (preferably, a silicone polyoxamide block copolymer), neoprene, and combinations thereof. Preferred viscoelastic liquids include mineral oil-modified block copolymers, hydrogels, and combinations thereof.

Such viscoelastic solids and liquids can be prepared by known methods. Many are commercially available.

Materials that are suitable for use as the above-referenced elastic component of the sound barrier of the invention include essentially all elastic materials. Preferred elastic materials, however, include those having a longitudinal speed of sound that is at least about 2000 meters per second (m/s).

Useful classes of elastic solids include metals (and alloys thereof), glassy polymers (for example, cured epoxy resin), and the like, and combinations thereof. Preferred classes of elastic solids include metals, metal alloys, glassy polymers, and combinations thereof (more preferably, copper, aluminum, epoxy resin, copper alloys, aluminum alloys, and combinations thereof; even more preferably, copper, aluminum, copper alloys, aluminum alloys, and combinations thereof; yet more preferably, aluminum, aluminum alloys, and combinations thereof; most preferably, aluminum).

Such elastic materials can be prepared or obtained by known methods. Many are commercially available.

If desired, the sound barrier used in carrying out the process of the invention can optionally comprise other component materials. For example, the sound barrier can include more than one viscoelastic material (including one or more viscoelastic materials that do not have a speed of propagation of longitudinal sound wave that is at least about 30 times its speed of propagation of transverse sound wave, provided that at least one viscoelastic material in the sound barrier meets this criterion) and/or more than one of the above-described elastic materials. The sound barrier can optionally include one or more inviscid fluids.

Preparation of Sound Barrier

The sound barrier used in carrying out the process of the invention comprises a substantially periodic (one-, two-, or three-dimensional) array of structures disposed in a first medium having a first density, the structures being made of a second medium having a second density different from the first density, as described above. Such an array can be formed by using either an above-described viscoelastic material or an above-described elastic material (or, as an alternative to an elastic material, a second, different viscoelastic material) as the first medium and the other of the two as the second medium.

The resulting structure or phononic crystal can be a macroscopic construction (for example, having a size scale on the order of centimeters or millimeters or less). If desired, the phononic crystal can take the form of a spatially periodic lattice with uniformly-sized and uniformly-shaped inclusions at its lattice sites, surrounded by a material that forms a matrix between the inclusions. Design parameters for such structures include the type of lattice (for example, square, triangular, and so forth), the spacing between the lattice sites (the lattice constant), the make-up and shape of the unit cell (for example, the fractional area of the unit cell that is occupied by the inclusions—also known as f, the so-called "fill factor"), the physical properties of the inclusion and matrix materials (for example, density, Poisson ratio, modulus, and so forth), the shape of the inclusion (for example, rod, sphere, hollow rod, square pillar, and so forth), and the like. By controlling such design parameters, the frequency of the resulting band gap, the number of gaps, and their widths can be tuned, or, at a minimum, the level of transmission loss can be adjusted as a function of frequency.

Preferably, the substantially periodic array of structures is a one-dimensional array in the form of a multi-layer structure comprising alternating layers of the first and second media (and, if desired, further comprising one or more of the above-described optional components in the form of one or more layers; for example, an "ABCD" structure, an "ACDB" structure, an "ACBD" structure, and so forth can be formed from the first (A) and second (B) media and two additional components C and D). The total number of layers of the multi-layer structure can vary over a wide range, depending upon the particular materials that are utilized, the layer thicknesses, and the requirements of a particular acoustic application.

For example, the total number of layers of the multi-layer structure can range from as few as two layers to as high as hundreds of layers or more. Layer thicknesses can also vary widely (depending upon, for example, the desired periodicity) but are preferably on the order of centimeters or less (more preferably, on the order of millimeters or less; most preferably, less than or equal to about 10 mm). Such layer thicknesses and numbers of layers can provide phononic crystal structures having dimensions on the order of centimeters or less (preferably, less than or equal to about 100 mm; more preferably, less than or equal to about 50 mm; even more preferably, less than or equal to about 10 mm; most preferably, less than or equal to about 5 mm). If desired, the layers can be cleaned (for example, using surfactant compositions or isopropanol) prior to assembly of the structure, and one or more bonding agents (for example, adhesives or mechanical fasteners) can optionally be utilized (provided that there is no significant interference with the desired acoustics).

A preferred embodiment of the multi-layer structure comprises from about 3 to about 10 (more preferably, from about 3 to about 5) alternating layers of viscoelastic material (preferably, silicone rubber, acrylate polymer, or a combination thereof) having a layer thickness of about 0.75 mm to about 1.25 mm and an elastic material (preferably, aluminum, epoxy resin, aluminum alloy, or a combination thereof) having a layer thickness of about 0.025 mm to about 1 mm. This can provide a phononic crystal structure having preferred dimensions on the order of about 1 mm to about 10 mm (more preferably, about 2 mm to about 4 mm; most preferably, about 2 mm to about 3 mm).

Preparation and Use of Hearing Protection Device

Hearing protection devices suitable for use in the process of the invention include those that comprise (a) at least one of the above-described sound barriers; and (b) at least one casing that at least partially encloses the sound barrier and is adapted for contact (direct or indirect) with the human ear. Preferably, the hearing protection device is an acoustic earmuff device, and/or the substantially periodic array of structures of the sound barrier of the hearing protection device is a one-dimensional array in the form of a multi-layer structure comprising alternating layers of the first and second media.

Useful acoustic earmuff devices include those that comprise (a) a connecting band having opposing first and second ends; and (b) a pair of earmuff cup assemblies connected to the opposing first and second ends of the connecting band, each earmuff cup assembly comprising at least one of the above-described sound barriers (and thus serving as a casing for the sound barrier). The connecting band can be, for example, a generally U-shaped band made of a flexible and/or resilient material (for example, two resilient wires held in substantially parallel alignment by a strip of flexible material such as a rubber or a plastic). The earmuff cup assembly can comprise, for example, an earcup (for example, a rigid earcup), the sound barrier, and, optionally, an earmuff cushion (for example, a polymer foam) and/or an earmuff cup liner (for example, an open cell polymer foam). The earmuff cup assemblies can be attached to the connecting band in essentially any desired manner.

Alternatively, the connecting band can be omitted, and the earmuff cup assemblies of the acoustic earmuff device can be provided with, for example, a skin adhesive for maintaining contact of the device with the human ear. Such acoustic earmuff devices can be re-usable (for example, through the use of replacement adhesive) or even disposable.

Other hearing protection devices (for example, acoustic earplug devices comprising a casing such as a polymer foam that is suitable for insertion in the human ear) and other types or designs of acoustic earmuff devices also can be used in carrying out the process of the invention. The sound barrier can be directly or indirectly (for example, through other device component(s)) attached to or suspended within the casing of the hearing protection device by essentially any known or hereafter-developed method (for example, use of adhesives, mechanical fasteners, form-fitting, and/or the like) that does not unacceptably disrupt or alter the substantial periodicity of the sound barrier or its acoustical characteristics.

The hearing protection device can be used in the hearing protection or sound insulation process of the invention by interposing or placing the hearing protection device between an acoustic source (preferably, a source of audible acoustic frequencies) and an acoustic receiver in the form of a human ear (a receiver of audible acoustic frequencies; preferably, in a manner such that the receiver is completely covered by the device). Useful acoustic sources include industrial noise, construction noise, recreational noise, music, and the like (preferably, noises or other sounds having an audible component; more preferably, noises or other sounds having a frequency component in the range of about 500 Hz to about 1500 Hz). The hearing protection device can be positioned between the source and the receiver such that a major face of the sound barrier of the device intercepts and thereby attenuates sound waves passing from the source to the receiver.

Those skilled in the art will be familiar with a variety of ways in which such devices can be so positioned. Normal incidence of the sound waves (relative to a major face of the sound barrier of the device) is generally preferred, although field incidence conditions (random orientation) can also provide reasonably effective acoustical attenuation (for example, with increases of no more than about 5 dB in transmission, relative to normal incidence conditions, when a one-dimensional, multi-layer sound barrier is utilized). If desired, the sound barrier of the hearing protection device can be used as an acoustic absorber (for example, by positioning the sound barrier relative to a substrate (for example, a rigid earcup of an earmuff cup assembly) such that it can function as a Helmholtz resonator-type absorber).

The hearing protection process and device of the invention can be used to achieve transmission loss across a relatively large portion of the audible range (with preferred embodiments providing a transmission loss that is greater than or equal to about 20 dB across the range of about 800 Hz to about 4000 Hz; with more preferred embodiments providing a transmission loss that is greater than or equal to about 20 dB across the range of about 500 Hz to about 4000 Hz; with even more preferred embodiments providing a transmission loss that is greater than or equal to about 20 dB across the range of about 250 Hz to about 4000 Hz; and with most preferred embodiments providing substantially total transmission loss across at least a portion of the range of about 500 Hz to about 4000 Hz). Such transmission losses can be achieved while maintaining phononic crystal structure dimensions on the order of centimeters or less (preferably, less than or equal to about 20 cm; more preferably, on the order of millimeters or less; most preferably, on the order of about 1 to about 3 mm).

In addition to one or more of the above-described sound barriers, the hearing protection device can optionally further comprise one or more conventional or hereafter-developed sound insulators (for example, conventional absorbers, barriers, and the like). If desired, such conventional sound insulators can be layered, for example, to broaden the frequency effectiveness range of the device.

EXAMPLES

Objects and advantages of this invention are further illustrated by the following examples, but the particular materials and amounts thereof recited in these examples, as well as other conditions and details, should not be construed to unduly limit this invention. All parts, percentages, ratios, and the like in the examples are by weight, unless noted otherwise. Solvents and other reagents were obtained from Sigma-Aldrich Chemical Company, St. Louis, Mo. unless otherwise noted.

Materials

Silicone Rubber: Item number 86915K24 available from McMaster-Carr Inc., Elmhurst, Ill., durometer hardness 40 A, thickness 0.8 mm, with adhesive backing, steady shear plateau modulus of $4.3 \times 10^5$ Pa at room temperature of 22.7° C. determined essentially as described below Aluminum: Aluminum foil, thickness 0.03 mm, sold commercially under the brand name of Reynolds Wrap™, available from Alcoa Corp., Pittsburgh, Pa.

Test Methods

Rheological Measurements

Rheological properties (for example, steady shear plateau modulus) were determined by carrying out linear, isothermal frequency sweep Dynamic Mechanical Analysis (DMA) tests in extensional mode on a test sample of material in a commercial ARES dynamic rheometer (available through TA Instruments of New Castle, Del.). The resulting data were then shifted using the Time-Temperature Superposition Principle to yield dynamic master curves at a selected reference temperature (taken as room temperature of 22.7° C.). The horizontal shift factors that were used for the shifting of the dynamic master curves were checked and found to obey the Williams-Landel-Ferry (WLF) form. The resulting dynamic master curves were finally converted to steady linear extensional modulus master curves at room temperature (22.7° C.) by means of the Ninomiya-Ferry (NF) procedure. The value of the rubbery tensile modulus plateau was determined from the steady linear extensional modulus master curve, and the steady shear plateau modulus of the material was taken to be one-third of the rubbery extensional modulus plateau value. (See, for example, the discussion of rheological data analysis techniques by John D. Ferry in *Viscoelastic Properties of Polymers*, $2^{nd}$ Edition, John Wiley & Sons, Inc., New York (1980).)

Sound Attenuation Measurements

The sound attenuation capabilities of various types of earmuffs were tested. The earmuffs included the following:

(a) a standard pair of 3M™ General Purpose Ear Muffs Model No. 1435 (available from 3M Company, St. Paul, Minn.; hereinafter, "1435 earmuffs") comprising an adjustable connecting band with two attached earmuff cup assemblies, each assembly comprising a rigid earcup made of 1 mm thick acrylonitrile/butadiene/styrene (ABS) polymer, and each earcup containing a single layer of green polyurethane closed cell foam (15 mm in thickness) as an acoustical attenuator insert;

(b) a modified pair of the 1435 earmuffs having an approximately 40 mm by 70 mm hole cut in the outside surface (surface not adjacent to ear of wearer) of each rigid earcup and in the foam layer, and having a two-layer sound barrier (consisting of two layers of the above-described silicone rubber; having a total thickness of 1.6 mm and other dimensions of about 45 mm by 75 mm, so that it was slightly larger than the hole and would not pop out) placed inside each earcup so as to fit snugly over the hole; and (c) a modified pair of the 1435 earmuffs having an approximately 40 mm by 70 mm hole cut in the outside surface (surface not adjacent to ear of wearer) of each rigid earcup and in the foam layer, and having a three-layer sound barrier (consisting of two layers of the above-described silicone rubber separated by an intervening or interposed layer of the above-described aluminum; having a total thickness of 1.63 mm and other dimensions of about 45 mm by 75 mm, so that it was slightly larger than the hole and would not pop out) placed inside each earcup so as to fit snugly over the hole. The measurements were carried out by using a Head and Torso Simulator Type 4128C (Brüel & Kjær, Sound & Vibration Measurement A/S, Denmark) with a PULSE Type 3109 front-end data acquisition system (Brüel & Kjær).

The earmuffs were placed on the Head and Torso Simulator (HaTS), which consisted of a head mounted on a torso (both having the international average dimensions of a human adult). Sound attenuation data was acquired using the PULSE front-end system, which consisted of a personal computer (PC) with a local area network (LAN) interface, PULSE Labshop™ software (Brüel & Kjær), and Windows XP™ operating system (Microsoft Corporation, Seattle, Wash.). In airborne acoustic measurements, the HaTS/PULSE system has been demonstrated to provide a correct simulation of the acoustic field around a human head and torso, as shown in its compliance with standards and its specifications (Brüel and Kjaer Product Data Sheet, Head and Torso Simulator—Type 4128C; Brüel and Kjaer PULSE Hardware System Data Sheet).

In carrying out the sound attenuation measurements, pink noise (sound having a frequency spectrum such that its power spectral density is proportional to the reciprocal of frequency) from four (4) speakers was introduced to the HaTS in a room measuring 3.04 meters by 3.96 meters (10 feet by 13 feet), with the HaTS positioned in the center of the room. A baseline measurement was made with no earmuffs on the HaTS. The level of noise was confirmed to be about 80 dBA (that is, units of the A-weighted decibel scale) of pink noise using the PULSE Labshop™ software and recorded. Then a pair of earmuffs was placed on the HaTS (while making note of the exact positioning of the earmuffs on the head of the HaTS and of the exact positioning of the earmuff cup assemblies of the earmuffs on the adjustable connecting band of the earmuffs). Then, the same amount of noise that had been used for the baseline measurement (that is, 80 dBA of pink noise) was introduced to the HaTS with earmuffs. The noise level was measured (for a sufficient duration that the Fast Fourier Transform (FFT) of the time signal could be at a steady state) and recorded. The earmuffs were then removed from the HaTS and replaced (with the same positioning as previously) for a total of five (5) trials.

The above-described procedure was repeated for each pair of earmuffs. When testing each pair of modified earmuffs, the multilayer inserts were taken out of the earmuff cup assemblies between trials and were re-inserted before replacing and repositioning the earmuffs on the HaTS.

Example 1 and Comparative Examples C-1 and C-2

Figure 2:
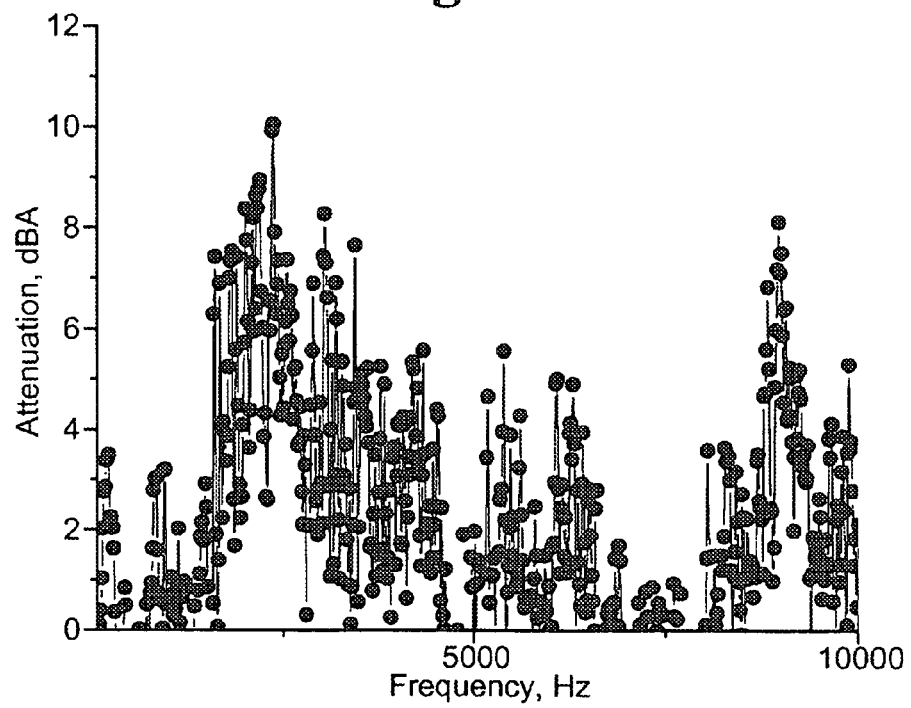
FIG. 2 is a plot of sound attenuation (in dBA) versus frequency (in Hz) for the embodiment of the process (and device) of the invention described in Example 1 and for the comparative process (and device) of Comparative Example 2.
Figure 3:
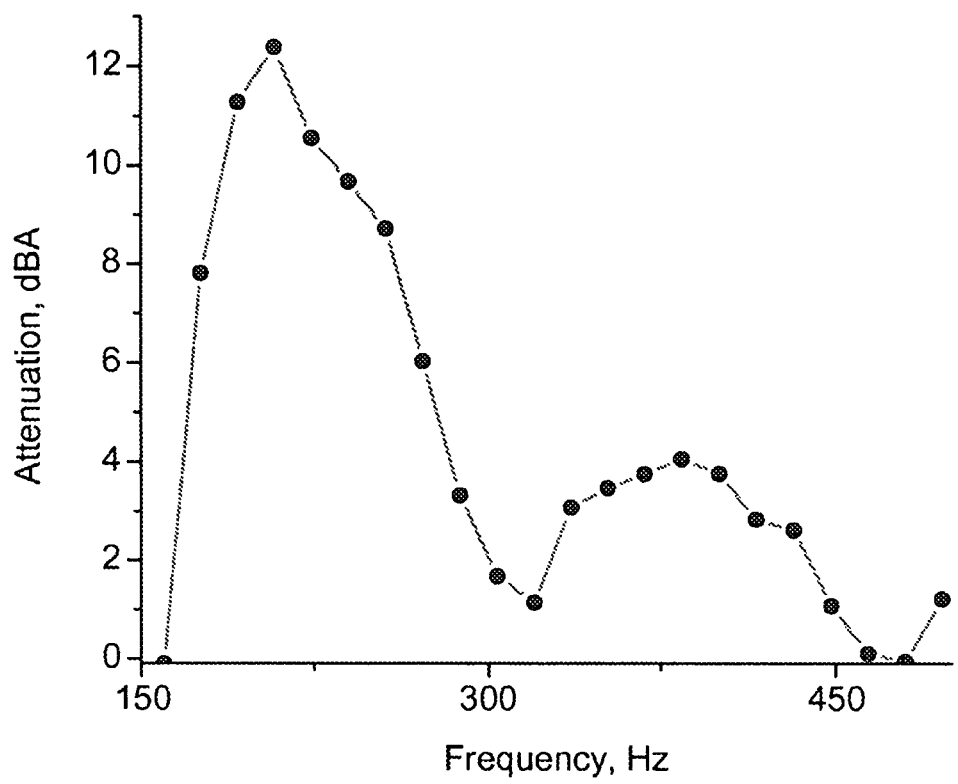
FIG. 3 is a plot of sound attenuation (in dBA) versus frequency (in Hz) for the embodiment of the process (and device) of the invention described in Example 1 and for the comparative process (and device) of Comparative Example 1.

The sound attenuation properties of the three above-described pairs of earmuffs were tested essentially according to the above-described procedure, and the results are shown in FIGS. 1-3.

TABLE 1

| Example No. | Layer Structure of Acoustical Attenuator Insert of Earmuffs (A = Silicone Rubber; B = Aluminum; C = Polyurethane Closed Cell Foam) |
|---|---|
| 1 | ABA |
| C-1 | AA |
| C-2 | C |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows:

We claim:

1. A process comprising (a) providing at least one hearing protection device comprising at least one sound barrier comprising at least one substantially periodic array of structures disposed in a first medium having a first density, said structures being made of a second medium having a second density different from said first density, wherein one of said first and second media is a viscoelastic medium having a speed of propagation of longitudinal sound wave and a speed of propagation of transverse sound wave, said speed of propagation of longitudinal sound wave being at least 30 times said speed of propagation of transverse sound wave, and wherein the other of said first and second media is a viscoelastic or elastic medium; and (b) interposing said hearing protection device between an acoustic source and an acoustic receiver in the form of a human ear.

2. The process of claim 1, wherein said viscoelastic medium is selected from viscoelastic solids, viscoelastic liquids, and combinations thereof.

3. The process of claim 2, wherein said viscoelastic solids and said viscoelastic liquids are selected from rubbery polymer compositions and combinations thereof.

4. The process of claim 3, wherein said rubbery polymer compositions are selected from elastomers, elastoviscous liquids, and combinations thereof.

5. The process of claim 1, wherein said other of said first and second media is an elastic medium.

6. The process of claim 5, wherein said elastic medium is an elastic solid selected from metals, metal alloys, glassy polymers, and combinations thereof.

7. The process of claim 1, wherein said substantially periodic array of structures is a one-dimensional array in the form of a multi-layer structure comprising alternating layers of said first and second media.

8. The process of claim 7, wherein said multi-layer structure comprises alternating layers of a viscoelastic medium and an elastic medium, said viscoelastic medium being selected from elastomers and combinations thereof, and said elastic medium being selected from metals, metal alloys, glassy polymers, and combinations thereof.

9. The process of claim 8, wherein said viscoelastic medium is selected from silicone rubbers, (meth)acrylate polymers, block copolymers, cellulosic polymers, blends of organic polymer and polydiorganosiloxane polyamide block copolymer, neoprene, and combinations thereof; and said elastic medium is selected from copper, aluminum, copper alloys, aluminum alloys, and combinations thereof.

10. The process of claim 7, wherein said multi-layer structure comprises from 3 to 10 alternating layers of a viscoelastic material having a layer thickness of 0.75 mm to 1.25 mm and an elastic material having a layer thickness of 0.025 to 1 mm, said multi-layer structure having dimensions in the range of 1 mm to 10 mm.

11. The process of claim 10, wherein said multi-layer structure comprises from 3 to 5 alternating layers of said viscoelastic material and said elastic material; said viscoelastic material being selected from silicone rubbers, acrylate polymers, and combinations thereof; said elastic material being selected from aluminum, epoxy resins, aluminum alloys, and combinations thereof; and said multi-layer structure having dimensions in the range of 2 mm to 4 mm.

12. The process of claim 1, wherein said sound barrier provides a transmission loss that is greater than or equal to 20 dB across the range of 800 Hz to 4000 Hz and has all dimensions less than or equal to 20 cm in size.

13. The process of claim 7, wherein said sound barrier provides a transmission loss that is greater than or equal to 20 dB across the range of 800 Hz to 4000 Hz and has all dimensions less than or equal to 20 cm in size.

14. The process of claim 1, wherein said sound barrier is used as an acoustic absorber.

15. The process of claim 1, wherein said hearing protection device further comprises at least one casing that at least partially encloses said sound barrier and is adapted for contact with the human ear.

16. The process of claim 1, wherein said hearing protection device is an acoustic earmuff device.

17. A process comprising (a) providing at least one acoustic earmuff device comprising at least one sound barrier comprising at least one one-dimensional, substantially periodic array of structures in the form of a multi-layer structure comprising alternating layers of a first medium having a first density and a second medium having a second density different from said first density, wherein one of said first and second media is a viscoelastic medium having a speed of propagation of longitudinal sound wave and a speed of propagation of transverse sound wave, said speed of propagation of longitudinal sound wave being at least 30 times said speed of propagation of transverse sound wave, and wherein the other of said first and second media is a viscoelastic or elastic medium;

and (b) interposing said hearing acoustic earmuff device between an acoustic source and an acoustic receiver in the form of a human ear.

18. The process of claim 17, wherein said first medium is a silicone rubber and said second medium is aluminum.

19. A hearing protection device comprising (a) at least one sound barrier comprising at least one substantially periodic array of structures disposed in a first medium having a first density, said structures being made of a second medium having a second density different from said first density, wherein one of said first and second media is a viscoelastic medium having a speed of propagation of longitudinal sound wave and a speed of propagation of transverse sound wave, said speed of propagation of longitudinal sound wave being at least about 30 times said speed of propagation of transverse sound wave, and wherein the other of said first and second media is a viscoelastic or elastic medium; and (b) at least one casing that at least partially encloses said sound barrier and is adapted for contact with the human ear.

20. The hearing protection device of claim 19, wherein said hearing protection device is an acoustic earmuff device, and/or said substantially periodic array of structures is a one-dimensional array in the form of a multi-layer structure comprising alternating layers of said first and second media.

* * * * *